(12) United States Patent
Wang et al.

(10) Patent No.: US 8,466,337 B2
(45) Date of Patent: Jun. 18, 2013

(54) BIODEGRADABLE AND BREATHABLE FILM

(75) Inventors: James H. Wang, Appleton, WI (US); Bo Shi, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 578 days.

(21) Appl. No.: 12/644,735

(22) Filed: Dec. 22, 2009

(65) Prior Publication Data

US 2011/0152815 A1 Jun. 23, 2011

(51) Int. Cl.
*A61F 13/514* (2006.01)
*B32B 3/26* (2006.01)

(52) U.S. Cl.
USPC .... 604/372; 604/370; 604/385.01; 428/304.4

(58) Field of Classification Search
USPC ...................................................... 604/385.01
See application file for complete search history.

(56) References Cited

U.S. PATENT DOCUMENTS

| | | |
|---|---|---|
| 4,454,268 A | 6/1984 | Otey et al. |
| 5,256,711 A | 10/1993 | Tokiwa et al. |
| 5,407,979 A | 4/1995 | Wu et al. |
| 5,500,465 A | 3/1996 | Krishnan et al. |
| 5,703,160 A | 12/1997 | Dehennau et al. |
| 5,922,379 A | 7/1999 | Wang |
| 6,231,970 B1 | 5/2001 | Andersen et al. |
| 6,235,815 B1 | 5/2001 | Loercks et al. |
| 6,656,581 B2 | 12/2003 | Wu et al. |
| 6,709,526 B1 | 3/2004 | Bailey et al. |
| 7,067,596 B2 | 6/2006 | Bastioli et al. |
| 7,077,994 B2 | 7/2006 | Bond et al. |
| 7,153,569 B2 | 12/2006 | Kaufman et al. |
| 7,214,414 B2 | 5/2007 | Khemani et al. |
| 7,384,588 B2 | 6/2008 | Gordon et al. |
| 8,227,658 B2 | 7/2012 | Shi et al. |
| 2002/0098341 A1 * | 7/2002 | Schiffer et al. ............... 428/323 |
| 2003/0015826 A1 | 1/2003 | Topolkaraev et al. |
| 2003/0021973 A1 | 1/2003 | Topolkaraev et al. |
| 2003/0108701 A1 * | 6/2003 | Bond et al. ................... 428/35.7 |
| 2003/0162013 A1 | 8/2003 | Topolkaraev et al. |
| 2005/0112350 A1 | 5/2005 | Ning |
| 2005/0112363 A1 | 5/2005 | Ning |
| 2006/0020056 A1 * | 1/2006 | Dombrowski et al. ........ 523/210 |
| 2007/0129467 A1 | 6/2007 | Scheer |
| 2008/0038496 A1 | 2/2008 | Bastioli et al. |
| 2008/0044650 A1 | 2/2008 | Sukigara et al. |
| 2008/0147034 A1 | 6/2008 | Wang et al. |

(Continued)

FOREIGN PATENT DOCUMENTS

WO      WO 02/42365      5/2002

OTHER PUBLICATIONS

Ralston, B.E., and T.A. Osswald, "The History of Tomorrow's Materials: Protein-Based Biopolymers," *Plastics Engineering*, Feb. 2008, vol. 64, No. 2, pp. 36-40.

(Continued)

*Primary Examiner* — Susan Su
(74) *Attorney, Agent, or Firm* — Dority & Manning, P.A.

(57) ABSTRACT

Breathable and biodegradable polymeric film materials of the invention are highly suitable for use in personal care absorbent articles and other articles. The film includes a biodegradable polymer resin, a thermoplastic starch, a filler and optionally, a protein. The breathable film has a renewable natural polymer component.

18 Claims, 5 Drawing Sheets

U.S. PATENT DOCUMENTS

| | | | |
|---|---|---|---|
| 2009/0054548 A1* | 2/2009 | Wang et al. | 523/111 |
| 2009/0191780 A1 | 7/2009 | Schiffer et al. | |
| 2009/0247036 A1 | 10/2009 | Shi et al. | |
| 2010/0159203 A1 | 6/2010 | Shi et al. | |
| 2011/0177275 A1* | 7/2011 | Morris | 428/36.92 |
| 2011/0196071 A1* | 8/2011 | Mentink et al. | 524/51 |

OTHER PUBLICATIONS

Tomasik, Piotr and Christopher H. Schilling, "Chemical Modification of Starch," *Advances in Carbohydrate Chemistry and Biochemistry*, vol. 59, 2004, pp. 176-316.

* cited by examiner

BIODEGRADABLE AND BREATHABLE FILM

The present invention is generally related to biodegradable polymer film compositions and more particularly to breathable biodegradable polymer film compositions and articles incorporating same.

BACKGROUND OF THE INVENTION

Polymer films are useful in making a variety of disposable articles because they are relatively inexpensive to manufacture, and can be made to be strong, durable, flexible, soft, and a barrier to aqueous liquids. Examples of such disposable products or articles include, but are not limited to, medical and health care products such as surgical drapes, gowns and bandages, protective work wear garments such as coveralls and lab coats, and infant, child and adult personal care absorbent articles such as diapers, training pants, disposable swimwear, incontinence garments and pads, sanitary napkins, wipes and the like. Other uses of polymeric film materials include geotextiles. It is often highly desirable for polymeric films used in such product applications to be both liquid impervious and breathable.

It is known that breathable films can be prepared by blending an organic or inorganic incompatible filler with a polyolefin-based resin, which is then melted, film-formed and stretched. These films are mainly used as liquid barriers in disposable personal care products, which are discarded immediately after use. However, these breathable films prepared from the polyolefin-based resin are not made from renewable polymer resources and cannot be degraded in the natural environment.

There is an increasing demand for the incorporation of more recyclable and/or degradable components in disposable products, and the design of products that can be disposed of by means other than by incorporation into solid waste disposal facilities such as landfills. As such, there is a need for new materials for disposable absorbent products that generally retain their integrity and strength during use, but after such use, are more efficiently disposable. For example, the disposable absorbent product may be easily and efficiently disposed of by composting. Alternatively, the disposable absorbent product may be easily and efficiently disposed of to a liquid sewage system wherein the disposable absorbent product is capable of being degraded.

While it is possible to enhance the breathability and biodegradability of polymer films separately, enhancing the biodegradability of polymer films without diminishing the breathability of the films is difficult. For example, biodegradable films derived from copolyesters are known in the art. Although these films had high breathability, but they were made from petroleum-derived biodegradable polymers which do not contain any renewable polymer components such as renewable natural polymers.

Accordingly, there remains a need for a composition which can be used to manufacture a biodegradable film which is also breathable and contains a renewable component, for use in making disposable or single-use articles of manufacture.

SUMMARY OF THE INVENTION

In one aspect of the invention is a biodegradable, breathable film made with a thermoplastic starch, in an amount ranging from about 20% to about 30% by weight of the film. Further included is an inorganic filler or organic filler or a mixture of both; and a biodegradable polymer resin, wherein the stretched film has a WVTR of about 2000 to about 2800 according to the MOCON test described herein.

In another aspect of the invention is a method for manufacturing a biodegradable, breathable film having the steps of: a) forming a thermoplastic resin from starch, modified starch, or a mixture of starch and plant protein; b) melt blending the thermoplastic resin and a filler; and c) extruding the film from the melt blend and then stretching the film.

In yet another aspect of the invention is a personal care article comprising:
a sheet of biodegradable, breathable film comprising: a thermoplastic starch in an amount ranging from about 20% to about 30% by weight of the film; an inorganic filler or organic filler or a mixture of an inorganic and an organic filler; and a resin wherein the stretched film has a WVTR of about 2000 to about 2800 according to the MOCON test described herein.

DETAILED DESCRIPTION OF THE INVENTION

Definitions

Figure 1:
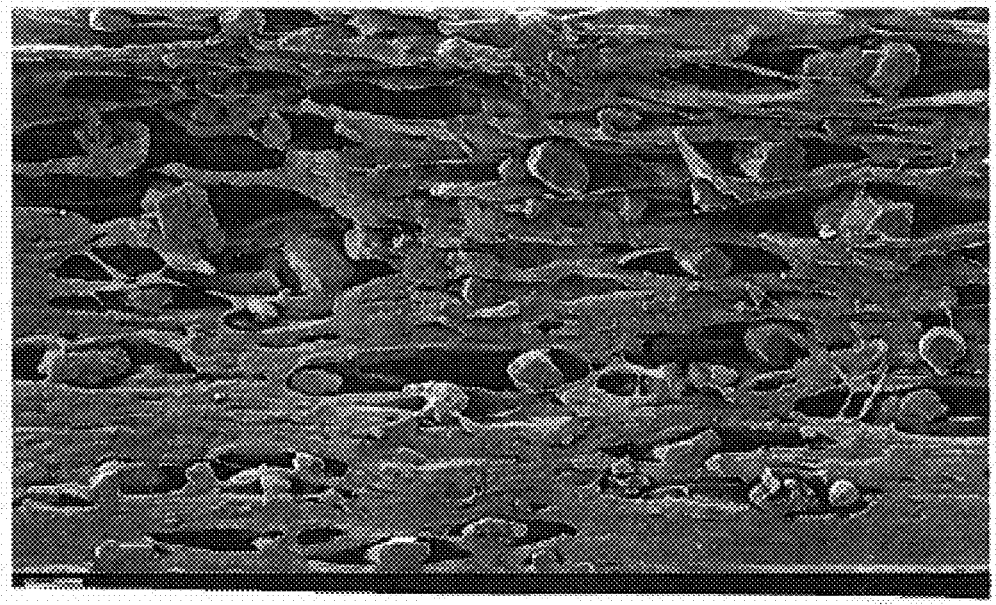
FIG. 1 is a micrograph of one embodiment of the present invention.

As used herein and in the claims, the term "comprising" is inclusive or open-ended and does not exclude additional unrecited elements, compositional components, or method steps. Accordingly, the term "comprising" encompasses the more restrictive terms "consisting essentially of" and "consisting of."

As used herein, "biodegradable" is meant to represent that a material degrades from exposure to air and/or water or from the action of naturally occurring microorganisms such as bacteria, fungi and algae.

As used herein, the term "stretched film" is meant to include films that have been stretched to create pores around a filler material. These stretched films are ready for use in an absorbent article as they will allow water vapor to pass therethrough.

As used herein, the term "breathability" refers to the water vapor transmission rate (WVTR) of an area of film. Breathability is measured in grams of water per square meter per day. For purposes of the present invention, a film is "breathable" if it has a WVTR of at least 800 grams per square meter per 24 hours as calculated using the MOCON® test method, which is described in detail below.

As used herein, the term "copolymer" generally includes but is not limited to, block, graft, random and alternating copolymers and blends and modifications thereof.

As used herein, the term "filler" is meant to include particulates and other forms of materials which can be added to the film blend and which will not chemically interfere with or adversely affect the extruded film but which are able to be uniformly dispersed throughout the film. Fillers known in the art include particulate inorganic materials such as for example talc, calcium carbonate, barium carbonate, magnesium carbonate, magnesium sulfate, titanium dioxide, mica, clays, kaolin, diatomaceous earth and the like, and organic particulate materials such as powdered polymers for example TEFLON, KEVLAR, crosslinked starch, and wood and other cellulose powders.

As used herein, the term "personal care product" means personal hygiene oriented items such as dry wipes, wet wipes, diapers, training pants, absorbent underpants, adult incontinence products, feminine hygiene products, and so forth.

The invention provides a composition made from a biodegradable copolyester, a biodegradable natural polymer, and a filler, the composition being suitable for manufacturing biodegradable films which are also breathable when stretched in either a monoaxial or biaxial direction. Such films have good mechanical and biodegradable properties as compared to films made from the copolyester alone.

Materials

The protein/starch thermoplastic compositions of the present invention further contain an organic or inorganic filler and an aliphatic-aromatic copolyester.

Protein:

The protein used in the protein/starch compositions within the scope of the present invention can be either plant or animal derived protein material. Gluten is most desired source of plant derived protein, in particular, wheat gluten. Wheat gluten protein may be purchased from Meelunie America, Inc. (Farmington, Mich.). Wheat gluten is composed of the water-insoluble prolamin and glutelin protein fractions known as gliadin and glutenin, respectively. The molecular weight of gliadin is in the range of 20,000 to 50,000 Dalton, while glutenin has an average molecular weight of 250,000 Dalton. It is glutenin that contributes to material elasticity.

Plant derived protein includes other gluten (such as oat, or rice gluten), corn zein, hordein, avenin, kafirin, or a combination thereof. Soy protein is yet another source of plant derived protein. Suitable soy protein includes soy protein meals, soy protein concentrate, soy protein isolate, or a combination thereof, such as those commercially available from Archer Daniels Midland Company (Decatur, Ill.); Protein Technologies International (St. Louis, Mo.); and Central Soya Company, Inc. (Fort Wayne, Ind.). Suitable animal derived protein includes casein, albumin, collagen, gelatin, keratin, or a combination thereof.

Starch:

The starch used in the protein/starch compositions within the scope of the present invention can be native (unmodified) starch, chemically modified starch, pregelatinized starch, or a combination thereof.

Starch is a natural polymer composed of amylose and amylopectin. Amylose is essentially a linear polymer having a molecular weight in the range of 100,000-500,000, whereas amylopectin is a highly branched polymer having a molecular weight of up to several million. Although starch is produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Broadly speaking, native (unmodified) and/or modified starches may be employed in the present invention. Modified starches, for instance, may be employed that have been chemically modified by typical processes known in the art (e.g., esterification, etherification, oxidation, enzymatic hydrolysis, etc.). Starch ethers and/or esters may be useful, such as hydroxyalkyl starches, carboxymethyl starches, etc. The hydroxyalkyl group of hydroxylalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch.

Regardless of whether it is in a native or modified form, the starch may contain different percentages of amylose and amylopectin, different size starch granules and different polymeric weights for amylose and amylopectin. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Such low amylose starches typically have a number average molecular weight ("$M_n$") ranging from about 50,000 to about 1,000,000 grams per mole, in some embodiments from about 75,000 to about 800,000 grams per mole, and in some embodiments, from about 100,000 to about 600,000 grams per mole, as well as a weight average molecular weight ("$M_w$") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("$M_w/M_n$"), i.e., the "polydispersity index", is also relatively high. For example, the polydispersity index may range from about 20 to about 100. The weight and number average molecular weights may be determined by methods known to those skilled in the art.

A plasticizer is also employed in the thermoplastic starch to help render the starch melt-processable. Starches, for instance, normally exist in the form of granules that have a coating or outer membrane that encapsulates the more water-soluble amylose and amylopectin chains within the interior of the granule. When heated, plasticizers may soften and penetrate the outer membrane and cause the inner starch chains to absorb water and swell. This swelling will, at some point, cause the outer shell to rupture and result in an irreversible destructurization of the starch granule. Once destructurized, the starch polymer chains containing amylose and amylopectin polymers, which are initially compressed within the granules, will stretch out and form a generally disordered intermingling of polymer chains. Upon resolidification, however, the chains may reorient themselves to form crystalline or amorphous solids having varying strengths depending on the orientation of the starch polymer chains. Because the starch is thus capable of melting and resolidifying at certain temperatures, it is generally considered a "thermoplastic starch."

Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight plasticizer is preferred, such as less than about 20,000 g/mol, preferably less than about 5,000 g/mol and more preferably less than about 1,000 g/mol.

The most desirable starch is native corn starch such as that purchased from Cargill, Inc. (Minneapolis, Minn.). Its molecular weight is determined using conventional gel permeation chromatography in dimethyl sulfoxide (DMSO), and is 16,600 for a number-averaged molecular weight, and 6,380,000 for weight-averaged molecular weight. The starch polydispersity index is about 37. Other starch materials such as the modified starch and GLUCOSOL 800 polymer may be purchased from Chemstar (Minneapolis, Minn.). These starch materials can be used for creating examples herein. The averaged molecular weight, of GLUCOSOL 800 as determined by gel permeation chromatography ("GPC"), is 2,900,000 with a polydispersity index estimated at 28. The GLUCOSOL 800 is soluble in aqueous solutions.

Biodegradable Polymer:

A biodegradable polymer, such as an aliphatic polyester such as polybutylene succinate (PBS), polyethylene succinate (PES), polylactic acid, polyhydroxybutyrate, polylactone, etc., an aliphatic-aromatic copolyester composed of three monomers: butanediol, adipic acid, and terephthalic acid; may be used for the purpose of enhancing natural polymers such as starch. The material is biodegradable and commercially available (e.g. ECOFLEX F BX 7011 produced by BASF, Ludwigshafen, Germany).

In one particular embodiment, for example, the first aliphatic-aromatic copolyester may comprise the following structure:

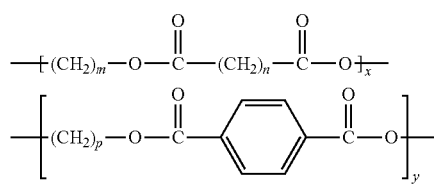

wherein m is an integer from 2 to 10, in some embodiments from 2 to 4, and in one embodiment, 4; n is an integer from 0 to 18, in some embodiments from 2 to 4, and in one embodiment, 4; p is an integer from 2 to 10, in some embodiments from 2 to 4, and in one embodiment, 4; x is an integer greater than 1, and in some embodiments, from 2 to 100; and y is an integer greater than 1, and in some embodiments from 2 to 100. One example of such a copolyester is polybutylene adipate terephthalate, which is commercially available under the designation ECOFLEX® F BX 7011 from BASF Corp. Another example of a suitable copolyester containing an aromatic terephthalic acid monomer constituent is available under the designation ENPOL™ 8060M from IRE Chemicals (South Korea). Other suitable aliphatic-aromatic copolyesters for use as the first copolyester may be described in U.S. Pat. Nos. 5,292,783; 5,446,079; 5,559,171; 5,580,911; 5,599,858; 5,817,721; 5,900,322; and 6,258,924, which are incorporated herein in their entirety by reference thereto for all purposes.

The first aliphatic-aromatic copolyester typically has a number average molecular weight ("$M_n$") ranging from about 40,000 to about 120,000 grams per mole, in some embodiments from about 50,000 to about 100,000 grams per mole, and in some embodiments, from about 60,000 to about 85,000 grams per mole. Likewise, the polymer also typically has a weight average molecular weight ("$M_w$") ranging from about 70,000 to about 360,000 grams per mole, in some embodiments from about 80,000 to about 250,000 grams per mole, and in some embodiments, from about 100,000 to about 200,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.2 to about 2.0, and in some embodiments, from about 1.4 to about 1.8. The weight and number average molecular weights may be determined by methods known to those skilled in the art. The melt flow index of the first aromatic-aliphatic polyester may also range from about 0.1 to about 10 grams per 10 minutes, in some embodiments from about 0.5 to about 8 grams per 10 minutes, and in some embodiments, from about 1 to about 5 grams per 10 minutes. The melt flow index is the weight of a polymer (in grams) that may be forced through an extrusion rheometer orifice (0.0825-inch diameter) when subjected to a load of 2160 grams in 10 minutes at a certain temperature (e.g., 190° C.), measured in accordance with ASTM Test Method D1238-E.

The first aliphatic-aromatic copolyester also typically has a melting point of from about 80° C. to about 140° C., in some embodiments from about 90° C. to about 130° C., and in some embodiments, from about 100° C. to about 120° C. The glass transition temperature ("$T_g$") of the copolyester is also relatively low to improve flexibility and processability of the polymers. For example, the $T_g$ may be about 25° C. or less, in some embodiments about 0° C. or less, and in some embodiments, about −10° C. or less. The melting temperature and glass transition temperature may be determined using differential scanning calorimetry ("DSC") in accordance with ASTM D-3417.

Filler:

A particulate filler material may enhance water vapor permeability of the film, thereby increasing the breathability of the film relative to an unfilled film. It is believed that a particulate filler material may create discontinuities, thus providing pathways for water vapor to move through the film. Particulate fillers may also increase the porosity of a film, and this porosity may be further increased during stretching of the film due to debonding between the filler and the polymer.

The filler particles can include any suitable inorganic or organic filler. The filler particles are preferably small, in order to maximize vapor transmission through the voids. Generally, the filler particles should have a mean particle diameter of about 0.1-10.0 micrometers, optionally about 0.5-5.0 micrometers, and optionally about 1.5-3.0 micrometers. Examples of organic fillers include starches, such as thermoplastic starches or pregelatinized starches, crosslinked starches, microcrystalline cellulose, and polymeric microbeads. Other Suitable fillers include, without limitation, calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. Calcium carbonate is a presently preferred filler material.

The filler particles may optionally be coated with a minor quantity (e.g. up to 2% by weight) of a fatty acid or other material to ease their dispersion in the polymer matrix prior to casting. Suitable fatty acids include without limitation stearic acid, or a larger chain fatty acid such as behenic acid. The amount of filler particles in the film should range from about 30% to about 80% (by weight film and filler particles), optionally from about 40% to about 70% (by weight of film and filler particles), and optionally from about 50% to about 65% (by weight film and filler particles), and optionally from about 50% to about 55% (by weight of film and filler particles).

Filler particles may be microporous. Microporous refers to a material that has pores, generally in the range of from about 2 Angstroms to about 50 Angstroms, that form a continuously interconnecting void space or network. The shape of the filler particle may be generally spherical or rounded. Other embodiments include plate-like, needle-like, or irregular shapes, points, or sharp edges.

Other additives and ingredients may be added to the film layer provided they do not seriously interfere with the ability of the film to be breathable or biodegradable. For example glycerin may be used as a plasticizer for converting native corn starch into thermoplastic starch. Glycerin may be obtained from Cognis Corporation (Cincinnati, Ohio). In addition to glycerin, a surfactant may be included. For example, a mono-di-glyceride, EXCEL P-40S, from Kao Corporation (Japan) may be used as a surfactant during thermoplastic starch processing.

Desirably, the filler is inorganic, such as micritic $CaCO_3$. This filler may be obtained from Specialty Minerals, Inc. (Bethlehem, Pa.), (MD 1517). The mean particle size for this filler is 2 microns. One advantage of using micritic calcium carbonate is that is has a tighter size distribution with few very fine particulates. Desirably, particles are coated with a 0.85% of a blend of stearic acid and palmitic acid (65/35).

Preparation of Polymer-Filler Blends

The thermoplastic starch of the present invention is formed by melt blending the components together in an extruder. Batch and/or continuous melt blending techniques may be employed in the present invention. For example, a mixer/kneader, Banbury mixer, Farrel continuous mixer, single-screw extruder, twin-screw extruder, roll mill, etc., may be utilized. One particularly suitable melt-blending device is a co-rotating, twin-screw extruder (e.g., USALAB twin-screw extruder available from Thermo Electron Corporation of Stone, England or an extruder available from Werner-Pfreiderer from Ramsey, N.J.). Such extruders may include feeding and venting ports and provide high intensity distributive and dispersive mixing. For example, a starch may be initially fed to a feeding port of the twin-screw extruder. Thereafter, a plasticizer and weak organic acid may be injected into the starch. Alternatively, the components may be simultaneously fed to the feed throat of the extruder or separately at a different point along its length.

Regardless, the materials are blended under high shear/pressure and heat to ensure sufficient mixing. For example, melt blending typically occurs at a temperature of from about 40° C. to about 160° C., in some embodiments, from about 50° C. to about 150° C., and in some embodiments, from about 60° C. to about 140° C. Likewise, the apparent shear rate during melt blending may range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

Film Formation

Films comprising the thermoplastic starch/protein, copolyesters and filler particles described herein and suitable for use in the absorbent articles described herein may be prepared utilizing any conventional film forming technique including extrusion casting and melt blowing. An extrusion casting technique may be used in combination with film annealing, film stretching, and/or heat setting after stretch operations.

In one embodiment, the polymer-filler blend is added to a single screw or twin screw extruder fitted with cast film die. The cast film made from the blend is stretched to form breathable films.

In a stretching operation, film is preferably stretched at temperatures from about 15° C. to about 50° C., optionally from about 25° C. to about 40° C., and optionally from about 30° C. to about 40° C. Cold stretching could improve void formation around filler particles, but may limit film stretchability. Optionally, film is stretched in two zones with optional heating to a range of from about 30° C. to about 50° C. between stretching zones. Either a single stretch zone or multiple stretch zones may be used. Films can be stretched uniaxially, biaxially, or both uniaxially and biaxially (at different times). Uniaxial stretching may be in the machine direction, the cross direction, or on a bias.

The stretch or draw ratio during stretching operation is from about 2.5 to about 10; e.g., the linear speed of the film exiting the stretching operation is 2.5 to 10 times the speed of the precursor film entering the stretching operation. Optionally, the stretch or draw ratio is from about 3.5 to about 7.

The thickness of the film may differ depending upon its uses and is generally in the range of from about 10 to about 300 micrometers.

The film has an elongation at break of at least about 240 percent, or about 400 percent or about 600 percent.

Test Methods

MOCON® Water Vapor Transmission Rate Test:

A suitable technique for determining the water vapor transmission rate (WVTR) value of a material is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the PERMATRAN-W® model 100K manufactured by Modern Controls, Inc (MOCON®) (Minneapolis, Minn.), USA. A first test is made of the WVTR of the guard film and air gap between an evaporator assembly that generates 100 percent relative humidity. Water vapor diffuses through the air gap and the guard film and then mixes with a dry gas flow which is proportional to water vapor concentration. The electrical signal is routed to a computer for processing. The computer calculates the transmission rate of the air gap and guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material.

This information is then used to calculate the transmission rate at which moisture is transmitted through the test material according to the equation:

$$TR^{-1}_{test\ material} = TR^{-1}_{test\ material, guardfilm, airgap} - TR^{-1}_{guardfilm, airgap}$$

The calculation of the WVTR uses the formula:

$$WVTR = F\rho_{sat}(T)RH/Ap_{sat}(T)(1-RH)$$

where:
F=the flow of water vapor in cc/min,
$\rho_{sat}(T)$=the density of water in saturated air at temperature T,
RH=the relative humidity at specified locations in the cell,
A=the cross sectional area of the cell, and
$p_{sat}(T)$=the saturation vapor pressure of water vapor at temperature T.

The invention will now be described in more detail by way of the following non-limiting examples, which are designed to illustrate particular aspects of the invention and teach one of ordinary skill in the art how to carry out the invention.

Tensile Strength

The tensile strength of the film of the present invention is tested according the "Standard Test Method for Tensile Properties of Plastics," ASTM 938-99, published by the American Society of Testing and Materials. The tensile strength of the breathable films, as shown in Table 6 for the blends described in Examples 3 through 6, as well as Examples 8 and 9, were determined on a SINTECH 1/D test machine, with five samples tested in both the machine direction (MD) and the cross direction (CD). The film samples were cut into dog-bone shapes with a center width of 3.0 mm before testing. The dog-bone film samples were held in place by grips on the SINTECH set to a gauge length of 18.0 mm. During the test, samples were stretched at a crosshead speed of 5.0 inches per minute until breakage occurred. The computer program, TESTWORKS 4, collected data during the test and generated a stress (MPa) versus strain (%) curve from which a variety of properties were determined: e.g., modulus, peak stress and elongation.

Material Blends

The materials noted thus far may be blended in different ways, and possibly, be blended in stages. For instance, the base material of Examples 1 and 2 is created. This base material may be blended with other examples as described herein.

The extrusion foaming conditions; such as extruder temperature profile, die pressure, feeding rate, screw speed, throughput rate, and take off speed; can be varied to control mechanical properties of the protein/starch/natural cellulosic fiber plastics.

EXAMPLE 1

Base Polymer of Thermoplastic Starch

A mixture of native corn starch and a surfactant (e.g. EXCEL P-40S, infra) can be created according to a ratio indicated in Table 1, Example 1. The blending may be performed in a 20" HOBART mixer (Hobart Corporation, Troy, Ohio) for 5 minutes. The mixture is then added to a feeder (e.g. a K-TRON gravimetric feeder, K-Tron America, Pitman, N.J.). The feeder hopper adds the materials into a co-rotating, twin screw extruder (e.g. a ZSK-30 extruder, Coperion Werner and Pfleiderer Corporation, Ramsey, N.J.). The extruder diameter is 30 mm with the length of the screws of up to 1328 mm. The extruder has 14 barrels, numbered consecutively 1~14 from the feed hopper to the die. The first barrel receives the mixture of starch and surfactant at a throughput rate of 10 lbs/hr when the extruder is heated to the temperature profile as shown in Table 1. The screw is set to rotate at 150 rpm. The glycerin is warmed up overnight to facilitate a pump delivery rate to achieve a 20% level of the base starch. In some cases, a vent is opened at the end of the extruder to release moisture.

Desirably, the die used to convert the starch to a thermoplastic starch has 3 openings of 5 mm in diameter. The openings are spaced apart by 3 mm. The thermoplastic starch strands exiting the die are cooled on a conveyer belt and pelletized for later blending.

TABLE 1

| Thermoplastic Starch Processing Conditions on ZSK-30 Extruder | | | | | | | | | | | | |
|---|---|---|---|---|---|---|---|---|---|---|---|---|
| Sample No. | Feeding Rate (lb/hr) | Native Corn Starch (%) | Excel P40S (%) | Extruder Speed (rpm) | Extruder Temperature Profile (° C.) | | | | | | | $P_{melt}$ (psi) | Torque (%) |
| | | | | | $T_1$ | $T_2$ | $T_3$ | $T_4$ | $T_5$ | $T_6$ | $T_7$ | $T_{melt}$ | | |
| Example 1 | 10 | 98 | 2 | 150 | 90 | 110 | 120 | 140 | 140 | 135 | 125 | 137 | 150~200 | 55~60 |

EXAMPLE 2

Base Polymer of Thermoplastic Starch and Gluten

This embodiment of the present invention is a mixture of the modified starch and wheat gluten. The mixture may be created at a 70/30 ratio of starch/gluten, respectively. In addition, 2% of a surfactant (e.g. EXCEL P-40S, infra) is added into the modified starch. The surfactant and wheat gluten are in powder form and are mixed in a mixer for about 5 minutes (e.g. a HOBART mixer). The mixture was then added to a feeder (e.g. K-TRON feeder, infra) that feeds the materials into a co-rotating, twin screw extruder (e.g. a ZSK-30 extruder, infra). The extruder diameter is 30 mm with the length of the screws up to 1328 mm. The extruder has 14 barrels, numbered consecutively 1-14 from the feed hopper to the die. The first barrel receives the mixture of starch and wheat gluten at 10 lbs/hr when the extruder is heated to the temperature profile as shown in Table 2. The screw is set to rotate at 150 rpm. Glycerin is pumped into extruder barrel 5 with a pressurized injector connected with a pump (such as an ELDEX brand pump, Napa, Calif.). The glycerin may be warmed up overnight to facilitate a pump delivery rate to achieve 20% level of the base starch in the blends as shown in Table 2. The vent is opened at the end of the extruder to release moisture. The die used to convert starch to thermoplastic starch has two openings of 7 mm in diameter which are separated by 13 mm. The thermoplastic modified starch/wheat gluten strands exiting the die are cooled on a conveyer belt and then pelletized.

EXAMPLE 7

The resin (such as ECOFLEX F BX 7011) is filled with calcium carbonate at a 50/50 ratio. The filled resin is prepared using a co-rotating, twin screw extruder (e.g. a ZSK-30 extruder, infra). The extruder diameter is 30 mm having a screw length of up to 1328 mm. The extruder has 14 barrels, numbered consecutively 1-14 from the feed hopper to the die. The resin is added to a feeder (e.g. a K-TRON brand feeder, infra) that vertically feeds the resin into the extruder. The first barrel receives the resin at 15 lbs/hr after the extruder is heated to the temperature profile of 130, 140, 150, 155, 155, 145, and 140° C., from zones 1 to 7 respectively. The screw is set to rotate at 150 rpm. A separate K-TRON feeder is later-

TABLE 2

Thermoplastic Starch and Gluten Processing Conditions on ZSK-30

| Sample No. | Starch/Gluten Ratio | Mixture Feeding Rate (lb/hr) | Glycerin (lb/hr) | Extruder Speed (rpm) | Extruder Temperature Profile (° C.) | | | | | | | | $P_{melt}$ (psi) | Torque (%) |
|---|---|---|---|---|---|---|---|---|---|---|---|---|---|---|
| | | | | | $T_1$ | $T_2$ | $T_3$ | $T_4$ | $T_5$ | $T_6$ | $T_7$ | $T_{melt}$ | | |
| Example 2 | 70/30 | 10 | 2.5 | 150 | 90 | 101 | 120 | 125 | 125 | 120 | 118 | 122 | 100~140 | 35~40 |

EXAMPLES 3-6

The blends for breathable films are made using an extruder (e.g. a ZSK-30 extruder, infra). The resin and thermoplastic starch from Example 1 are added to a feeder (e.g. a K-TRON gravimetric feeder, infra). The mixture of thermoplastic starch and resin using one gravimetric feeder is vertically fed the feedthroat of the extruder. The first extruder barrel received two resins at pre-determined ratios as shown in Table 3. The feed rate is 20 lbs/hr when the extruder is heated to the temperature profile as shown in Table 3 for Examples 3 through 6. Calcium carbonate filler was fed to the feed throat of the twin screw extruder by a K-TRON gravimetric feeder. The screw is set to rotate at 150 rpm. The vent is closed at the end of the extruder as there is no need to release moisture. A 3-hole die is used to shape the melted resin into strands that are later cooled on a conveyer belt and then pelletized for dry blending.

ally attached to the extruder at about ½ barrel length as a side feeder to deliver $CaCO_3$ filler at the 50% ratio. The melting point of the polymer is 160° C., the torque is 80~90%, and the pressure is 420~460 psi. The vent is closed at the end of the extruder as there is no need to release moisture. A 3-hole die was used to shape the melt into strands that were cooled on a conveyer belt and then pelletized for dry blending.

EXAMPLE 8

The filled resin from Example 7 and the thermoplastic modified starch/gluten from Example 2 are dry blended at a 50/50 ratio for film casting using a single screw extruder (such as a RHEOMEX 252 extruder available from HAAKE, Karlsruhe, Germany). The resulting film composition is 25% $CaCO_3$ filler, 15% thermoplastic modified starch and gluten, and 60% resin. The desired extruder temperature profiles from zone 1 to 5 are 135, 140, 140, 140, and 140° C. respec-

TABLE 3

Breathable Blend Processing Conditions on ZSK-30 Extruder

| Sample No. | Resin Feeding Rate (lb/hr) | Blend Composition | | | Extruder Speed (rpm) | Extruder Temperature Profile (° C.) | | | | | | | | $P_{melt}$ (psi) | Torque (%) |
|---|---|---|---|---|---|---|---|---|---|---|---|---|---|---|---|
| | | Corn TPS (lb/hr) | Ecoflex (lb/hr) | $CaCO_3$ (lb/hr) | | $T_1$ | $T_2$ | $T_3$ | $T_4$ | $T_5$ | $T_6$ | $T_7$ | $T_{melt}$ | | |
| Example 3 | 26.6 | 6 | 14 | 6.6 | 160 | 140 | 175 | 177 | 175 | 165 | 160 | 155 | 175 | 200~250 | 80~85 |
| Example 4 | 30.8 | 6 | 14 | 10.8 | 160 | 140 | 175 | 177 | 175 | 165 | 160 | 155 | 178 | 210~260 | 90~95 |
| Example 5 | 26.6 | 8 | 12 | 6.6 | 160 | 138 | 165 | 175 | 175 | 170 | 165 | 150 | 175 | 200~250 | 78~84 |
| Example 6 | 30.8 | 8 | 12 | 10.8 | 160 | 140 | 165 | 175 | 177 | 170 | 168 | 153 | 178 | 220~260 | 88~95 |

Referring still to Table 3, the resin feeding rate ranges from about 27 lb/hr to about 31 lb/hr. The calcium carbonate filler ranges from about 7 to about 11 lbs/hr. The calcium carbonate is delivered into the extruder through a separate feeder that is laterally attached to the feeder at about ½ the barrel length.

In another embodiment, the $CaCO_3$ filler may be incorporated into the resin first, and then blended with thermoplastic modified starch to create breathable blends. See Example 7 below.

tively. The die temperature is 140° C., and the melt temperature is 157° C. The die gap is 20 mils, and the pressure at the die is about 5600 psi. The pellet feeding rate is set at 60 rpm, with a torque that fluctuates within 4300~4400 m-g. The biodegradable and breathable film having a 2 mil thickness is made into a breathable and stretchable film. In comparison to those films without gluten, the processing temperature for film casting of Example 8 may be much lower than the processing temperatures shown in Examples 3 to 6.

EXAMPLE 9

The filled resin pellets from Example 7 and thermoplastic modified starch/gluten pellets from Example 2 are dry blended at a 70/30 ratio for film casting using single screw extruder (e.g. the Rheomex 252, infra). The resulting film composition is a blend of 15% $CaCO_3$ filler, 28% thermoplastic modified starch and gluten (Example 2), and 57% resin. The pump processing temperatures from zone 1 to 5 are 135, 140, 140, 140 respectively, and the die temperature is 140° C. The melt temperature is 156° C. The die gap is 20 mils. The pellet feeding rate is set at 60 rpm, with torque that may fluctuate around 4000~4200 m-g. The pressure at the die is about 5400 psi. The film is about 2 mil thickness and is a biodegradable and breathable film.

EXAMPLE 10

Exemplary Micrographs

By stretching the film of Example 9, void formation in the film is enhanced and hence the film is made more porous and breathable. Biaxial stretching of the film produces even greater void formation and hence enhanced breathability of the film.

Figure 2:
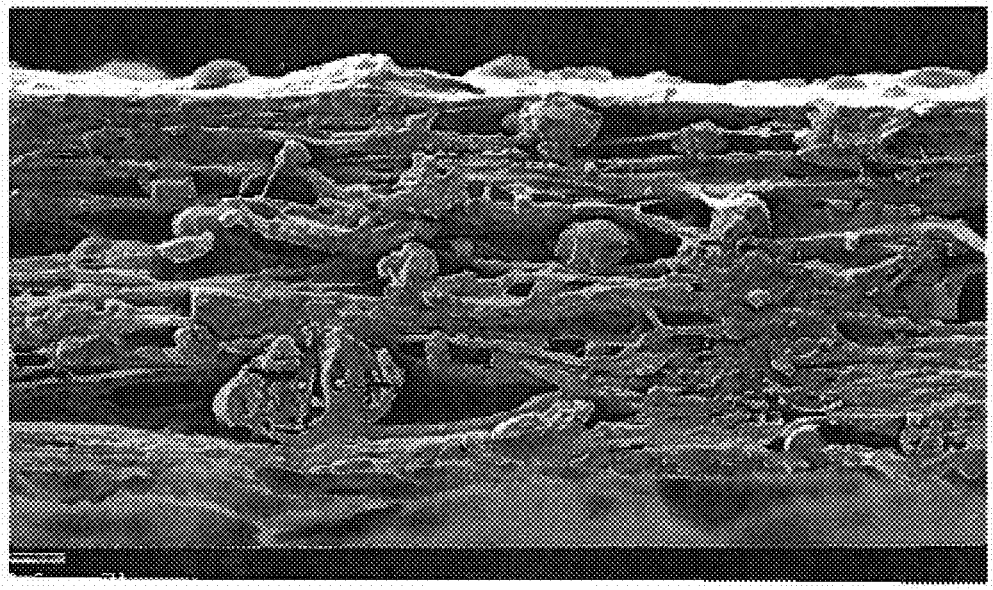
FIG. 2 is a micrograph of another embodiment of the present invention.

A few film samples are selected for a scanning electron microscopy (SEM) study. The photograph is obtained by a plasma etching/optical method using the standard secondary electron imaging mode achieved by a positive-biased detector (e.g. an EVERHART-THORNLEY detector). The results are shown in FIG. 1, which depicts the film 10 of Example 3 after an elongation in the machine direction 14 of 450%. Calcium carbonate 12 debonding is well displayed in SEM picture, indicating enhanced film breathability. FIG. 2 shows the film 20 of Example 5. Once again, zigzag paths 22 may be seen after a 380% elongation in the machine direction 24.

EXAMPLE 11

Oxidized wheat starch (e.g. PREGEL ADHERE 2000, purchased from MGP Ingredients, Inc., Atchison, Kans.) was oxidized using sodium hypochlorite in a suspension where the pH is maintained in the alkaline region. The equipment and processing steps to make the thermoplastic oxidized starch (TPOS) is the same as those shown in Example 1 except for the following conditions as noted: (1) the oxidized wheat starch is mixed with EXCEL P40S at a 98/2 ratio, (2) the resin feeding rate is 13 lb/hr., (3) the glycerin is 25% of the base starch, (4) the extruder vent is open, (5) temperature profile is 100, 125, 140, 140, 140, 130, 128° C. from zone 1 to zone 7 respectively, (6) the melt temperature is 160° C., (7) the melt pressure is 510~550 psi, (8) the torque is 38~42%, and (9) the screw rotational speed is 150 rpm.

EXAMPLES 12-14

The wheat based thermoplastic oxidized starch ("TPOS") of Example 11 is blended with ECOFLEX BX 7011 and a filler. Specifically, the blends for breathable films are made using an extruder (e.g. the ZSK-30 extruder, infra). The ECOFLEX F BX 7011 and the TPOS is added to an extruder feeder (e.g. the K-TRON feeder, infra). The first barrel is vertically fed with ECOFLEX F BX 7011 and TPOS at the pre-determined ratios shown in Table 4. The extruder is heated to the temperature profile as shown in Table 7 for Examples 12 through 14. The screw is set to rotate at 200 rpm. The filler (e.g. $CaCO_3$) is side-fed around a middle section of the extruder barrel. Without a need to release moisture, the vent is closed at the end of the extruder. A 3-hole die is used to shape the melt into strands that are cooled on a conveyer belt and then pelletized.

TABLE 4

| Sample No. | Resin Feeding Rate (lb/hr) | Blend Composition | | | Extruder Speed (rpm) | Extruder Temperature Profile (° C.) | | | | | | | | $P_{melt}$ (psi) | Torque (%) |
|---|---|---|---|---|---|---|---|---|---|---|---|---|---|---|---|
| | | TPOS (lb/hr) | Ecoflex (lb/hr) | $CaCO_3$ (lb/hr) | | $T_1$ | $T_2$ | $T_3$ | $T_4$ | $T_5$ | $T_6$ | $T_7$ | $T_{melt}$ | | |
| Example 12 | 10 | 3 | 7 | 0 | 200 | 100 | 118 | 142 | 149 | 146 | 145 | 161 | 184 | 170~190 | 78~85 |
| Example 13 | 15 | 3 | 7 | 5 | 200 | 100 | 120 | 134 | 168 | 147 | 145 | 154 | 175 | 170~190 | 90~95 |
| Example 14 | 17.6 | 3 | 7 | 7.6 | 200 | 100 | 120 | 142 | 158 | 146 | 145 | 151 | 172 | 240~250 | 90~97 |

The film casting is similar to those for the films described in Examples 3 to 9 except for the temperature conditions. The temperature conditions are 110, 120, 140, 140, 140° C. from zone 1 to zone 5, respectively.

Tensile Strength Table 5 summarizes the tensile strength for Examples 12-14. The film peak strength is relatively low for all films whether or not there is a filler. Example 12 is used as a control for the film containing TPOS, therefore, it is not stretched. In comparison to Example 12, the film elongation of Example 14 is at an unacceptable level when the $CaCO_3$ filler is presented at 43%.

TABLE 5

Mechanical Properties for Ecoflex and TPOS Films with or without Filler

| Sample | Sample Description | Composition | Film Thickness (mil) | | Modulus (Mpa) | | Peak Stress (MPa) | | Elongation (%) | |
|---|---|---|---|---|---|---|---|---|---|---|
| | | | MD | CD | MD | CD | MD | CD | MD | CD |
| Example 12 | Ecoflex/TPOS | 70/30 | 2.0 | 2.0 | 56 | 57 | 12 | 11 | 487 | 600 |
| Example 13 | Ecoflex/TPOS/CaCO3 | 46.9/20.1/33 | 2.4 | 2.6 | 215 | 231 | 8 | 7 | 189 | 243 |
| Example 14 | Ecoflex/TPOS/CaCO3 | 39.9/17.1/43 | 2.3 | 2.3 | 300 | 241 | 11 | 10 | 6 | 10 |

The film from Example 14 is not stretched because there is not enough elongation available for stretching. The film from Example 13 has CaCO$_3$ filler at 33%, and is stretched to 120% for the film breathability testing. The stretch was not even across the film, therefore some areas did not stretch. The film breathability tested is extremely high, at 12964 g/m$^2$/day. However, there are small holes observed during the film breathability testing. Nevertheless, one may refine the stretch to adjust the film breathability level as desired.

TABLE 6

Mechanical and Physical Properties

| | | | Film Mechanical Properties | | | | | | |
|---|---|---|---|---|---|---|---|---|---|
| | | | Film Thickness | | Modulus (MPa) | | Peak Stress (MPa) | | Elongation (%) | |
| Example No. | Sample Description | Composition | MD (mil) | CD (mil) | MD | CD | MD | CD | MD | CD |
| Example 3 | Ecoflex/TPS/CaCO3 | 52.5/22.5/25 | 1.75 | 1.75 | 181 | 209 | 27 | 22 | 460 | 640 |
| Example 4 | Ecoflex/TPS/CaCO3 | 45.5/19.5/35 | 1.69 | 1.66 | 210 | 200 | 20 | 14 | 399 | 550 |
| Example 5 | Ecoflex/TPS/CaCO3 | 45/30/25 | 1.71 | 1.65 | 189 | 185 | 21 | 11 | 464 | 460 |
| Example 6 | Ecoflex/TPS/CaCO3 | 39/26/35 | 1.59 | 1.69 | 213 | 238 | 14 | 10 | 270 | 349 |
| Example 8 | Ecoflex/TPSG/CaCO3 | 60/15/25 | 3.02 | 2.78 | 131 | 139 | 8 | 7 | 176 | 342 |
| Example 9 | Ecoflex/TPSG/CaCO3 | 57/28/15 | 2.36 | 2.44 | 131 | 133 | 12 | 6 | 323 | 229 |

As can be seen in Table 6, the starch content of Examples 3 and 4 is relatively low. The film elongation of Example 4 is 399% due to of the fact that there is more filler in Example 4 than in Example 3. The film elongation decreased appreciably in Example 6 when starch is higher with the same level of calcium carbonate filler is high with respect to the resin content. The film modulus for all examples is comparable. The film peak stress decreases steadily as either thermoplastic starch or filler in the examples increased, as expected. For the film containing a blend of starch and gluten shown in Examples 8 and 9, peak stress is roughly ½ of those films without the presence of gluten, although the film modulus and elongation are comparable.

Breathability:

In order to evaluate the film breathability, the film samples shown in Examples 3 through 6, and Example 9 were stretched in the machine direction under ambient and identical conditions. The level of the extension during film stretching is indicated in Table 7, including film breathability values determined by the MOCON test (STM 3806).

TABLE 7

Film Breathability

| Sample No. | % Stretch | MOCON (g/m2/day) |
|---|---|---|
| Example 3 | 0 | 824 |
| | 300 | 1261 |
| | 450 | 1323 |
| Example 4 | 0 | 849 |
| | 300 | 2073 |
| | 400 | 2342 |
| Example 5 | 0 | 1131 |
| | 300 | 2347 |
| | 380 | 2368 |
| Example 6 | 0 | 1292 |
| | 280 | 2803 |
| Example 9 | 0 | 898 |
| | 100 | 1279 |
| | 150 | 1270 |

The examples above indicate that a biodegradable film can be produced which as relatively good WVTR value and hence, good breathability. For instance, see Example 6, Table 7, which shows that at a 280 percent stretch there is a MOCON value of about 2800 g/m2/day. Further, the breathability of the films is markedly enhanced when the films are biaxially stretched. Such breathable and biodegradable films are highly useful for use in single-use or disposable articles and products where a fluid impervious barrier is required and a breathable barrier is desired. Examples of such products include, but are not limited to, medical and health care products such as surgical drapes, gowns and bandages, protective workwear garments such as coveralls and lab coats, and infant, child and adult personal care absorbent articles such as diapers, training pants, disposable swimwear, incontinence garments and pads, sanitary napkins, wipes and the like. Other uses for such breathable and biodegradable polymeric film materials may include geotextiles. While not described in detail herein, various additional potential processing and/or finishing steps known in the art such as aperturing, slitting, further stretching, treating, or lamination of the breathable and biodegradable polymeric film materials with other films or with nonwoven web layers, may be performed without departing from the spirit and scope of the invention.

Figure 3:
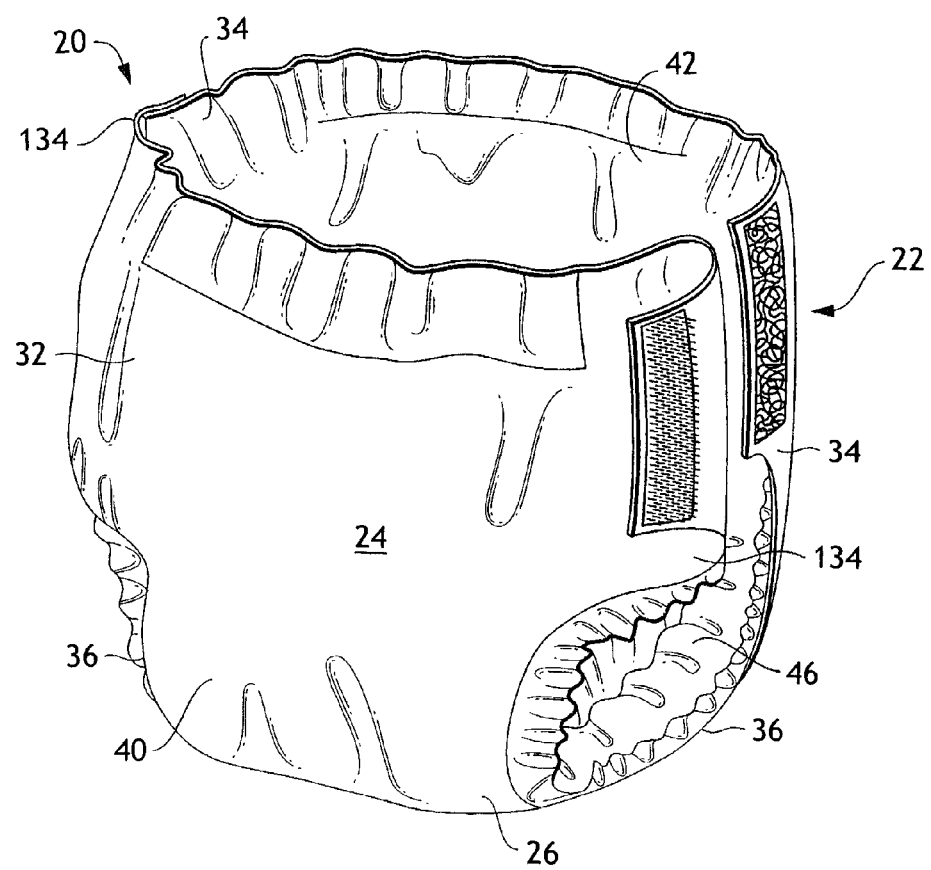
FIG. 3 is a perspective view of a disposable training pant made with the breathable and biodegradable film of the invention.
Figure 4:
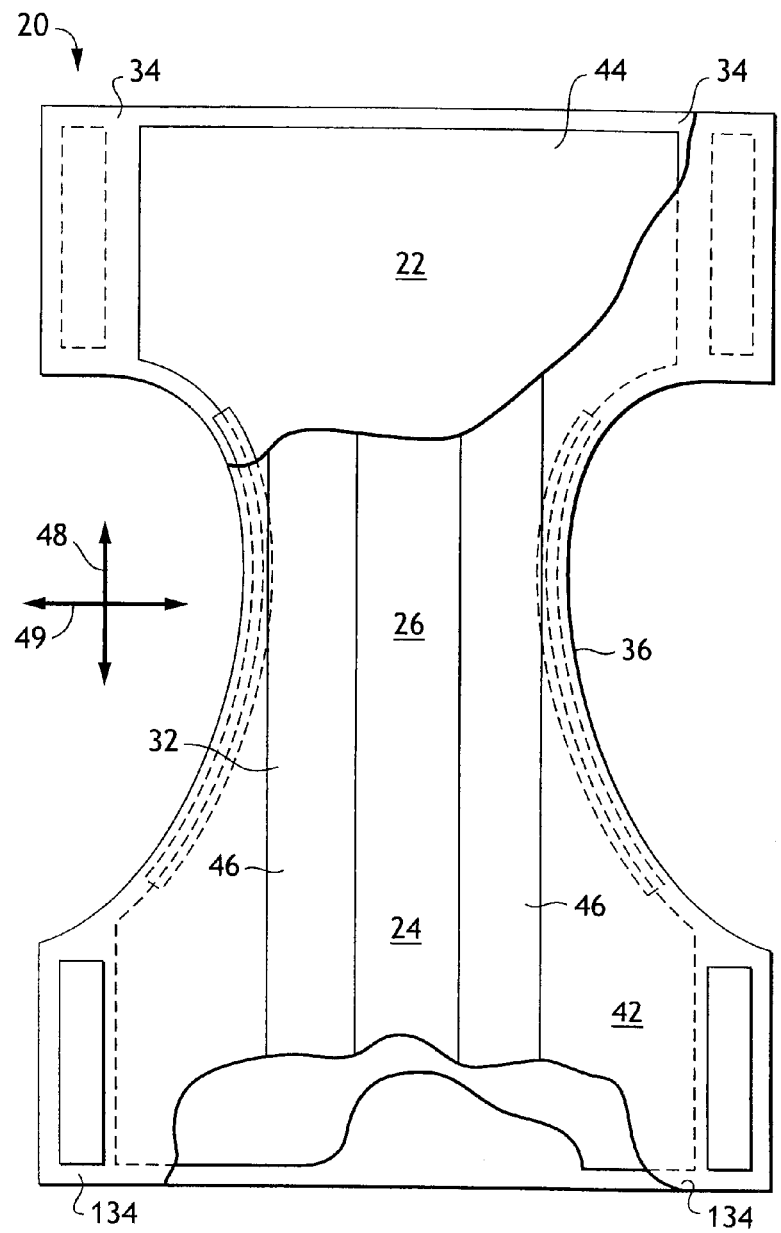
FIG. 4 is a plan view of the training pant shown in FIG. 3.
Figure 5A:
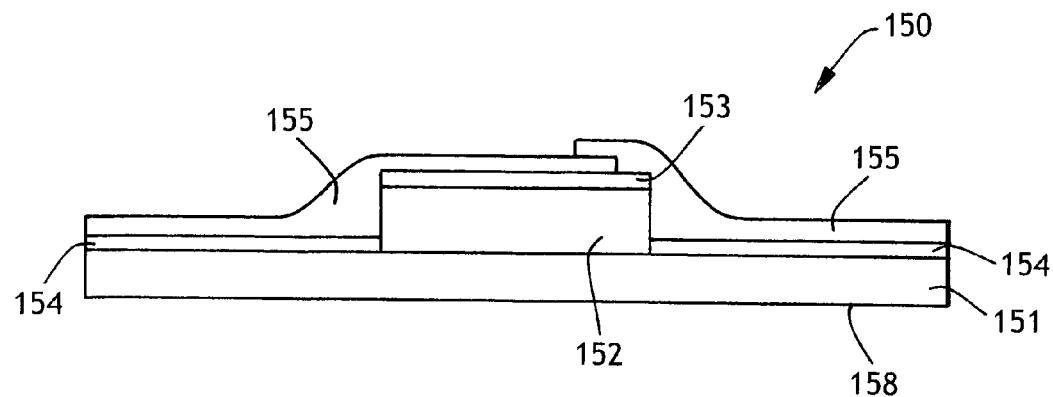
FIG. 5A is a cross sectional view of a bandage made with the breathable and biodegradable film of the invention.
Figure 5B:
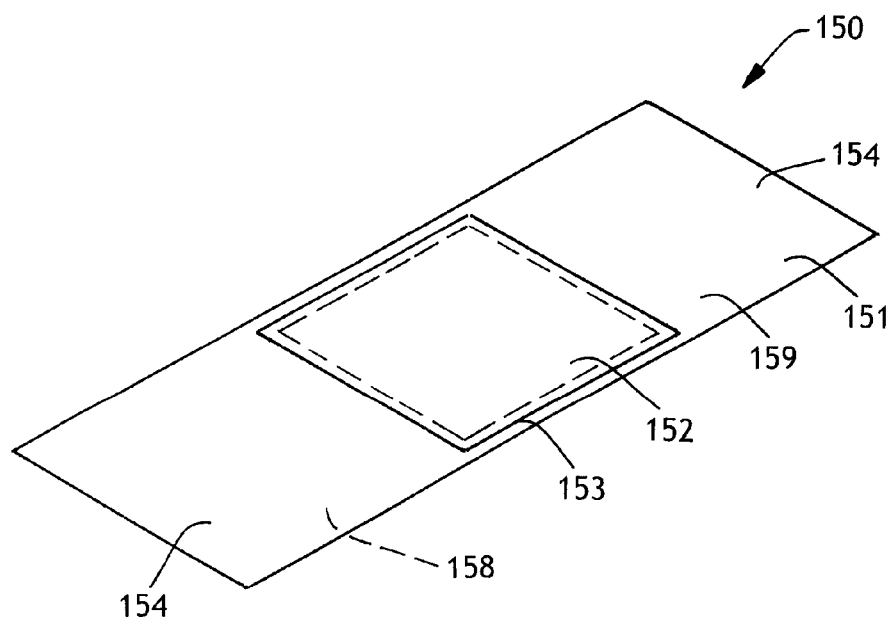
FIG. 5B is a perspective view of the bandage shown in FIG. 5A
Figure 6:
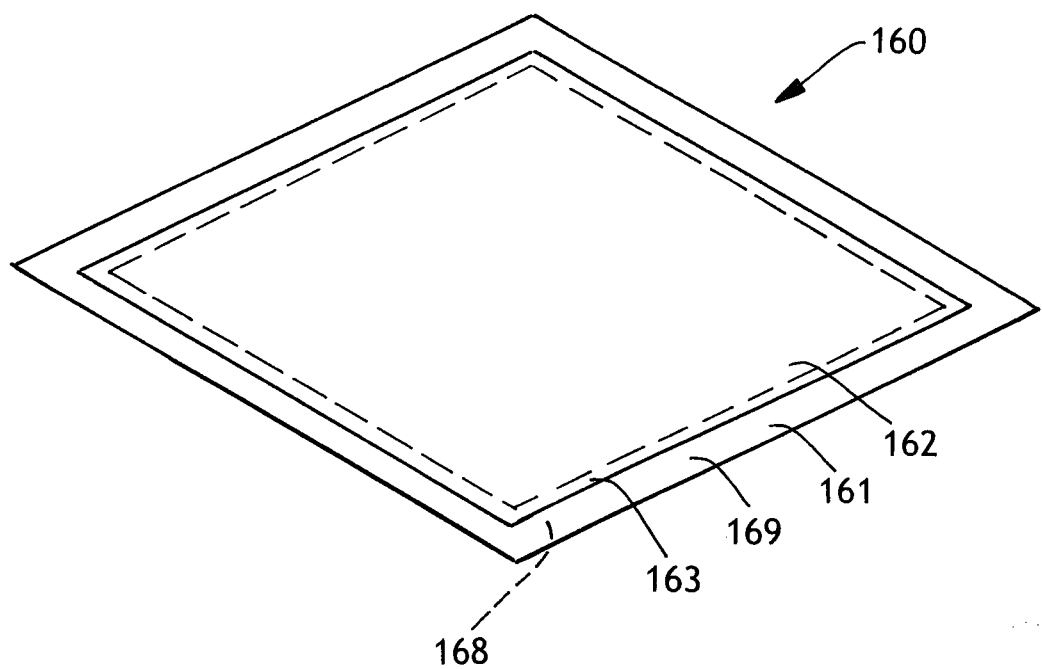
FIG. 6 is a perspective view of a bed pad made with the breathable film of the present invention.

Exemplary Application—A Training Pant:

To gain a better understanding of the present invention, attention is directed to FIG. 3 and FIG. 4 for exemplary purposes showing a training pant of the present invention. It is understood that the present invention is suitable for use with various other absorbent articles, including but not limited to other personal care absorbent articles, health/medical absorbent articles, household/industrial absorbent articles, sports/construction absorbent articles, and the like, without departing from the scope of the present invention.

Various materials and methods for constructing training pants are disclosed in U.S. Pat. No. 6,761,711 to Fletcher et al.; U.S. Pat. Nos. 4,940,464 to Van Gompel et al.; 5,766,389 to Brandon et al., and 6,645,190 to Olson et al., each of which is incorporated herein by reference in a manner that is consistent herewith.

FIG. 3 illustrates a training pant in a partially fastened condition, and FIG. 4 illustrates a training pant in an opened and unfolded state. The training pant defines a longitudinal direction 1 that extends from the front of the training pant when worn to the back of the training pant. Perpendicular to the longitudinal direction 1 is a lateral direction 2.

The pair of training pants defines a front region 22, a back region 24, and a crotch region 26 extending longitudinally between and interconnecting the front and back regions. The pant also defines an inner surface (i.e., body-facing surface) adapted in use (e.g., positioned relative to the other components of the pant) to be disposed toward the wearer, and an outer surface (i.e., garment-facing surface) opposite the inner surface. The training pant has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 134 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44 such as shown in FIG. 2 disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The topsheet 42 and the absorbent core 44 may be made from many different materials known to those skilled in the art. The two layers, for instance, may be extensible and/or elastically extensible. The backsheet 40, for instance, can be the biodegradable film of the present invention. See U.S. patent Ser. No. 11/796,585, incorporated herein to the extent it does not conflict with the present invention.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,969,378 to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. In general, a surge management layer helps to quickly acquire and diffuse surges or gushes of liquid that may be rapidly introduced into the absorbent structure of the article. The surge management layer can temporarily store the liquid prior to releasing it into the storage or retention portions of the absorbent core 44. Examples of suitable surge management layers are described in U.S. Pat. Nos. 5,486,166 to Bishop et al.; 5,490,846 to Ellis et al.; and 5,820,973 to Dodge et al., each of which is incorporated herein by reference in a manner that is consistent herewith.

The article 20 can further comprise an absorbent core 44. The absorbent core 44 may have any of a number of shapes. For example, it may have a 2-dimensional or 3-dimensional configuration, and may be rectangular shaped, triangular shaped, oval shaped, race-track shaped, 1-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core includes cellulose fiber and/or synthetic fiber, such as meltblown fiber, for example. Thus, in some aspects, a meltblown process can be utilized, such as to form the absorbent core in a coform line. In some aspects, the absorbent core 44 can have a significant amount of stretchability. For example, the absorbent core 44 can comprise a matrix of fibers which includes an operative amount of elastomeric polymer fibers. Other methods known in the art can include attaching superabsorbent polymer particles to a stretchable film, utilizing a nonwoven substrate having cuts or slits in its structure, and the like.

The absorbent core 44 can additionally or alternatively include absorbent and/or superabsorbent material. Accordingly, the absorbent core 44 can comprise a quantity of superabsorbent material and optionally fluff contained within a matrix of fibers. In some aspects, the total amount of superabsorbent material in the absorbent core 44 can be at least about 10% by weight of the core, such as at least about 30%, or at least about 60% by weight or at least about 90%, or between about 10% and about 98% by weight of the core, or between about 30% to about 90% by weight of the core to provide improved benefits. Optionally, the amount of superabsorbent material can be at least about 95% by weight of the core, such as up to 100% by weight of the core. In other aspects, the amount of absorbent fiber of the present invention in the absorbent core 44 can be at least about 5% by weight of the core, such as at least about 30%, or at least about 50% by weight of the core, or between about 5% and 90%, such as between about 10% and 70% or between 10% and 50% by weight of the core. In still other aspects, the absorbent core 44 can optionally comprise about 35% or less by weight unmodified fluff, such as about 20% or less, or 10% or less by weight unmodified fluff.

It should be understood that the present invention is not restricted to use with superabsorbent material and optionally fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include a foam.

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover or encompass all such modifications, alterations and/or changes.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, the film may be used as a packaging film or articles such as product bags, molded containers, bottles, etc. Accordingly, all modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

The invention claimed is:

1. A biodegradable, breathable film comprising:
   a thermoplastic starch, wherein the thermoplastic starch is present in an amount ranging from about 20% to about 30% by weight of the film;
   a filler selected from inorganic fillers, organic fillers, and mixtures thereof, wherein the filler is present in an amount ranging from about 25% to about 35% by weight of the film; and
   a biodegradable polymer resin comprising an aliphatic-aromatic copolyester that is polybutylene adipate terephthalate, wherein the biodegradable polymer resin is present in an amount ranging from about 39% to about 45% by weight of the film, wherein the film after stretching has a water vapor transmission rate of about 2000 g/m$^2$/day to about 2800 g/m$^2$/day.

2. The film of claim 1 wherein the inorganic filler is coated with a blend of stearic and palmitic acid.

3. The film of claim 1 further comprising a protein.

4. The film of claim 3 wherein the protein comprises a plant protein.

5. The film of claim 4 wherein the protein comprises gluten or soy protein.

6. The film of claim 4 wherein the plant protein ranges from 5% to about 45% by weight of the film.

7. The film of claim 1 wherein the thermoplastic starch is a thermoplastic hydroxypropyl starch.

8. The film of claim 1 wherein the inorganic and/or organic filler comprises particles having a mean size of 2 microns.

9. The film of claim 1 wherein the thermoplastic starch comprises a plasticizer.

10. The film of claim 9 wherein the plasticizer is a polyhydric alcohol.

11. The film of claim 9 wherein the plasticizer is glycerol or sorbitol.

12. The film of claim 9 wherein the plasticizer is a mixture of two or more plasticizers.

13. The film of claim 1, wherein the film has a percent elongation in the machine direction ranging from 176% to 464%.

14. An article comprising the film of claim 1 as a drape sheet.

15. An absorbent article comprising the film of claim 1 wherein the film is configured to be a backsheet.

16. The absorbent article of claim 15 comprising an absorbent core disposed between the backsheet and a body-side liner attached to the backsheet.

17. A method for manufacturing a biodegradable, breathable film comprising the steps of:
    a) forming a thermoplastic resin from a starch, a modified starch, or a mixture of starch and plant protein, wherein the thermoplastic resin is present in the film in an amount ranging from about 20% to about 30% by weight of the film;
    b) melt blending the thermoplastic resin with a filler selected from inorganic fillers, organic fillers, and mixtures thereof, wherein the filler is present in an amount ranging from about 25% to about 35% by weight of the film, and a biodegradable polymer resin comprising an aliphatic-aromatic copolyester that is polybutylene adipate terephthalate, wherein the biodegradable polymer resin is present in the film in an amount ranging from about 39% to about 45% by weight of the film; and
    c) extruding the film from the melt blend to form a film; and
    d) stretching the film wherein the film after stretching has a water vapor transmission rate of about 2000 g/m$^2$/day to about 2800 g/m$^2$/day.

18. The method of claim 17, wherein the film has a percent elongation in the machine direction ranging from 176% to 464%.

\* \* \* \* \*